United States Patent [19]
Kieturakis

[11] Patent Number: 5,653,722
[45] Date of Patent: Aug. 5, 1997

US005653722A

[54] ANTEROGRADE/RETROGRADE SPIRAL DISSECTOR AND METHOD OF USE IN VEIN GRAFTING

[76] Inventor: Maciej J. Kieturakis, 372 Beverly Dr., San Carlos, Calif. 94070

[21] Appl. No.: 367,705
[22] Filed: Jan. 3, 1995
[51] Int. Cl.⁶ ................................................. A61B 17/00
[52] U.S. Cl. ........................... 606/159; 606/170; 606/191
[58] Field of Search ................................. 606/167, 159, 606/170, 171, 190, 191, 192, 198, 207, 1; 604/96, 101, 104–106; 128/749–755, 859; 623/1, 12

[56] References Cited

U.S. PATENT DOCUMENTS

| | | | |
|---|---|---|---|
| 4,030,503 | 6/1977 | Clark, III | 606/159 |
| 4,653,496 | 3/1987 | Bundy et al. | 606/159 |
| 4,706,671 | 11/1987 | Weinrib | 606/159 |
| 4,793,346 | 12/1988 | Mindich . | |
| 4,909,781 | 3/1990 | Husted | 606/159 |
| 5,373,840 | 12/1994 | Knighton . | |
| 5,480,379 | 1/1996 | La Rosa | 606/159 |

FOREIGN PATENT DOCUMENTS 2082459   5/1980   United Kingdom .

*Primary Examiner*—Michael Buiz
*Assistant Examiner*—William Lewis
*Attorney, Agent, or Firm*—Townsend and Townsend and Crew LLP

[57] ABSTRACT

A surgical instrument for bluntly dissecting connective tissues in a plane around a vein or other anatomic structure in a minimally invasive surgery. An anterograde or retrograde spiral dissector comprises one or more elongate spiral members, each having a blunt distal tip adapted for helical advancement in a plane around the surface of a vein. Anterograde helical advancement of the spiral assembly bluntly dissects small diameter "guide paths" in connective tissues with little resistance to penetration. With the spiral dissector thus helically engaged, the instrument drives itself anterograde upon rotation. The spiral dissector includes a "path-expanding" structure associated with either a distal, medial or proximal region of each spiral member, by which is meant the path-expanding structure is adapted for anterograde or retrograde travel along the dissected "guide paths" to further expand the dimensions of the guide paths thereby to dissect the connective tissues in a 360° plane around the vein.

29 Claims, 11 Drawing Sheets

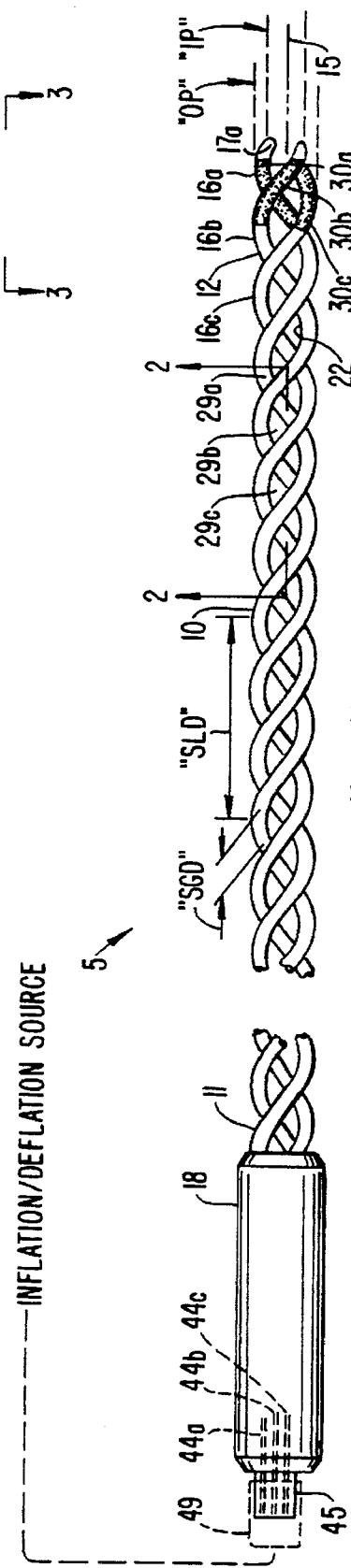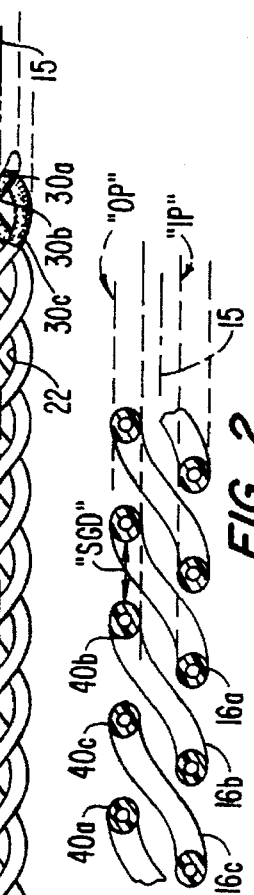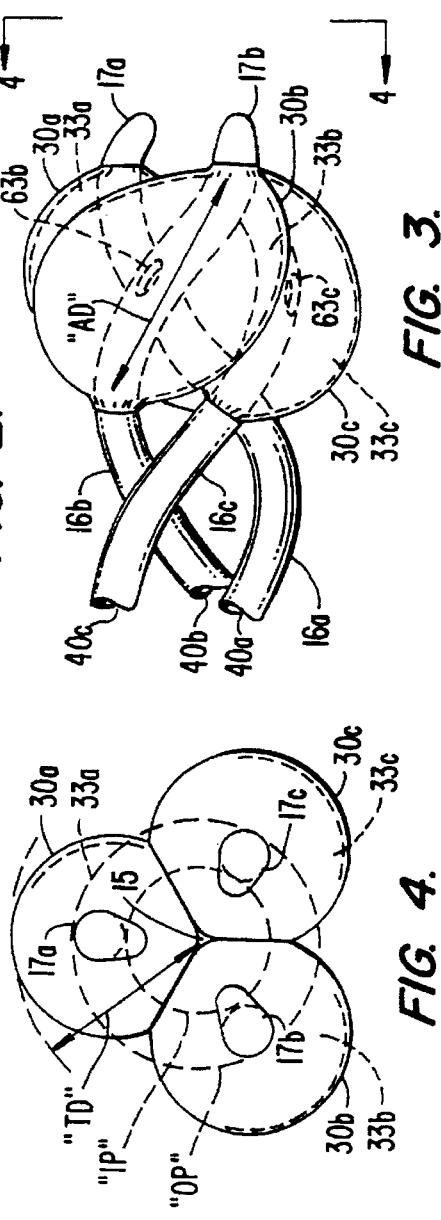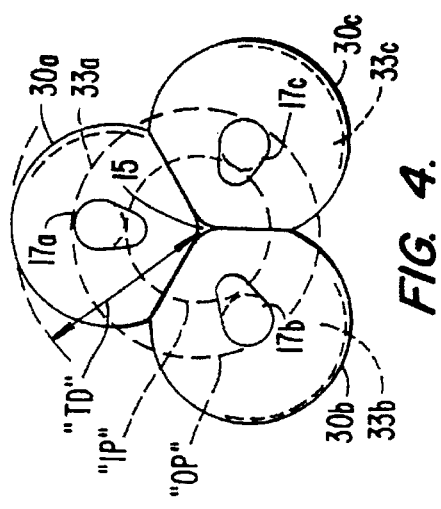

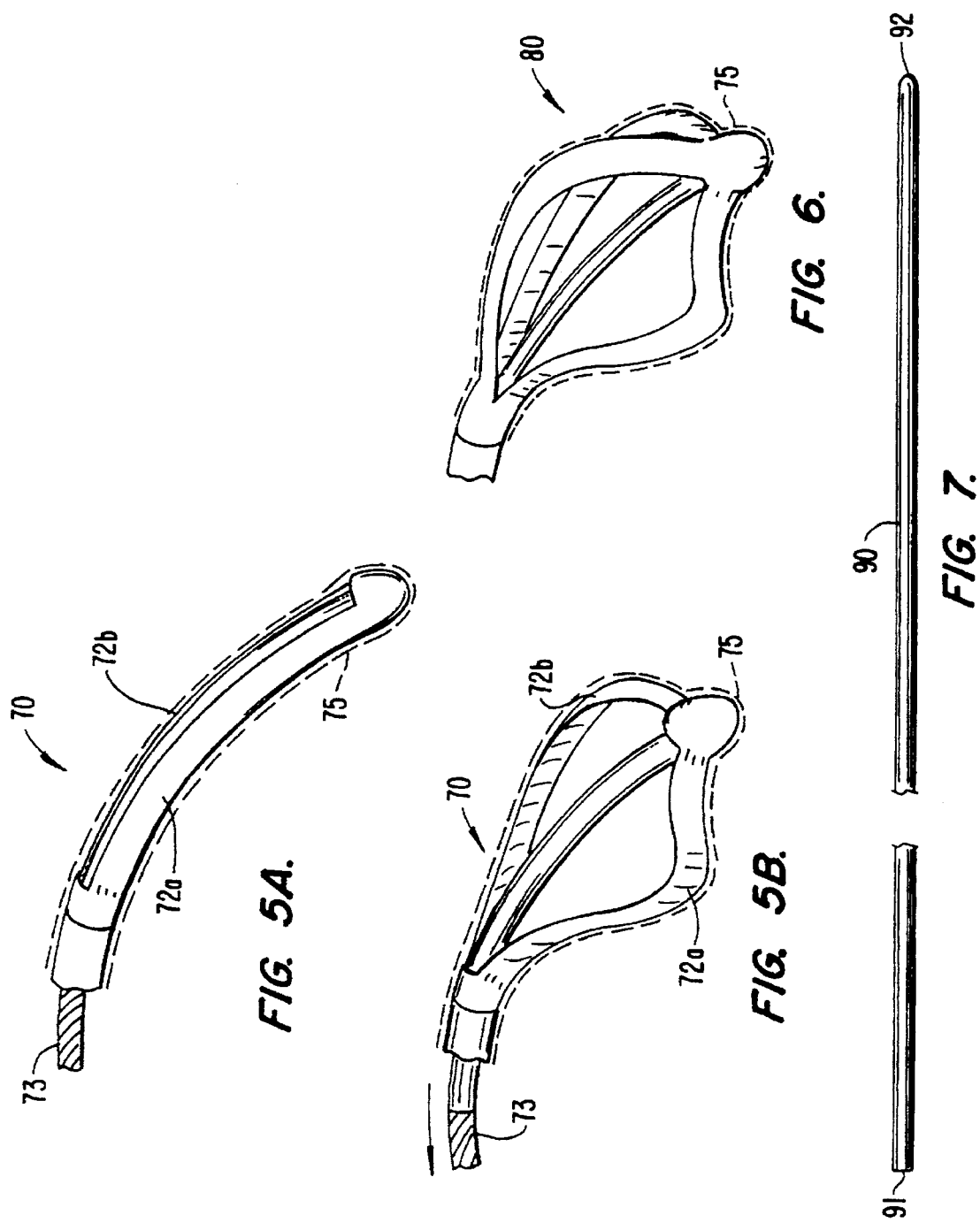

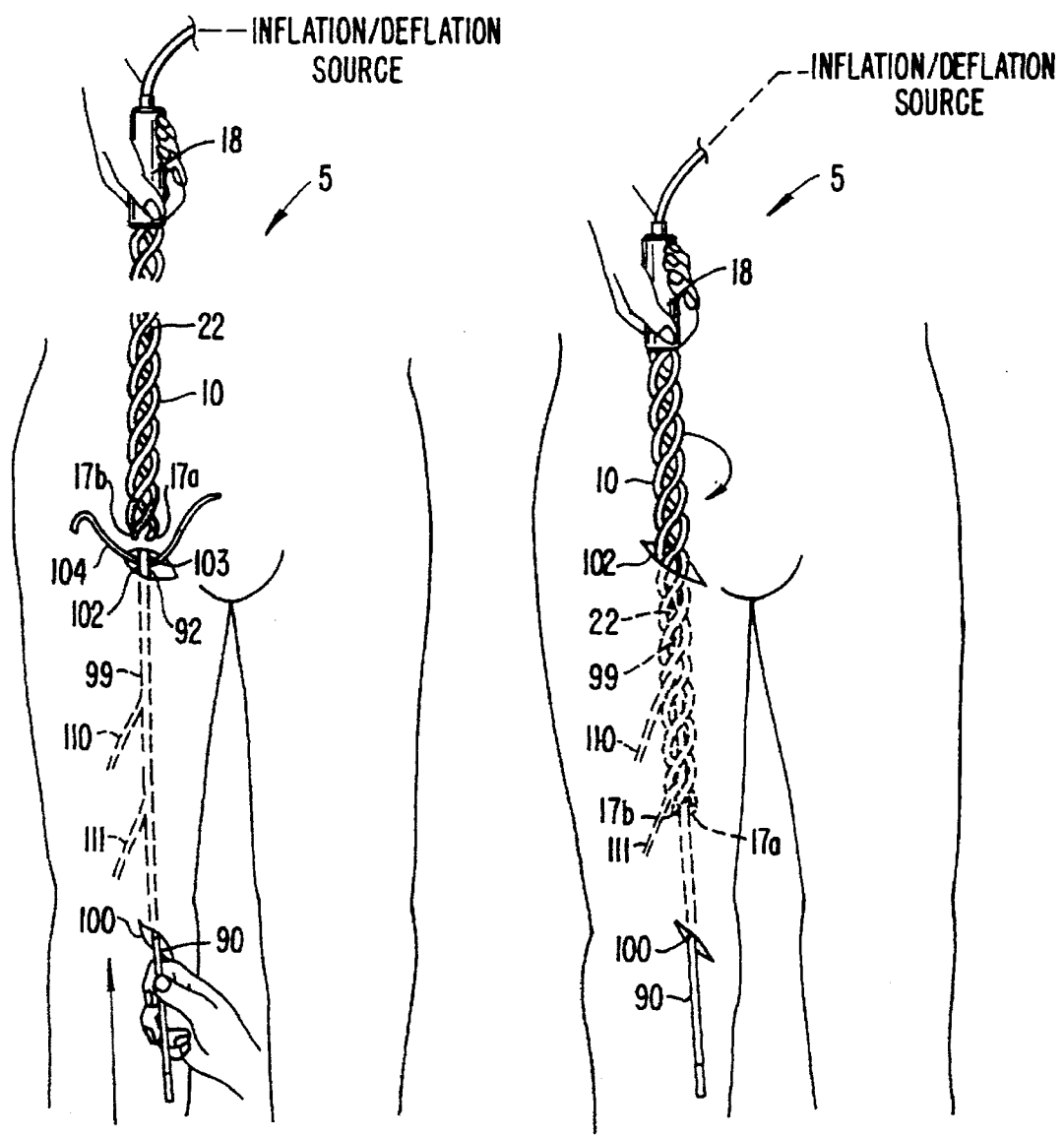

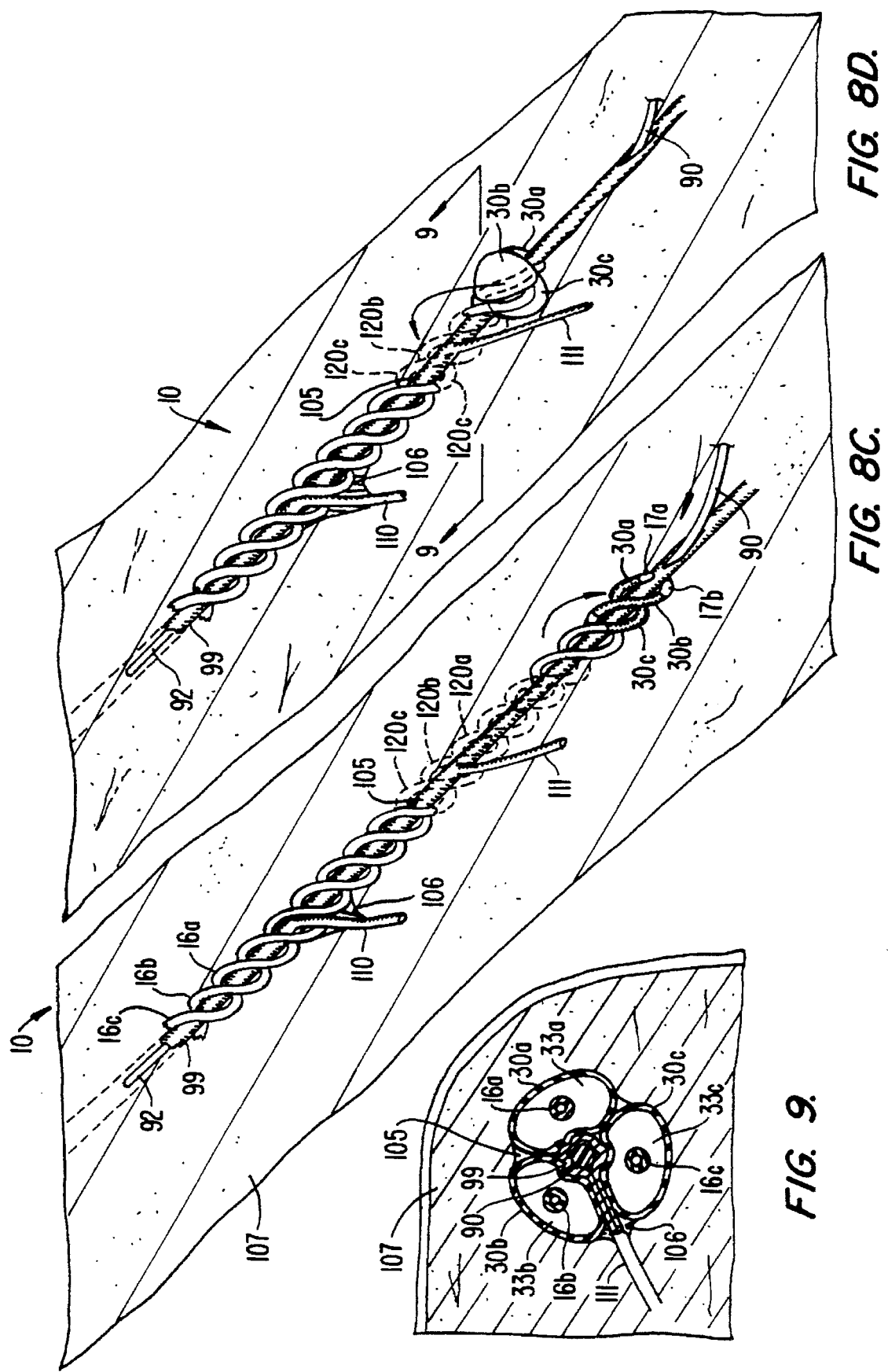

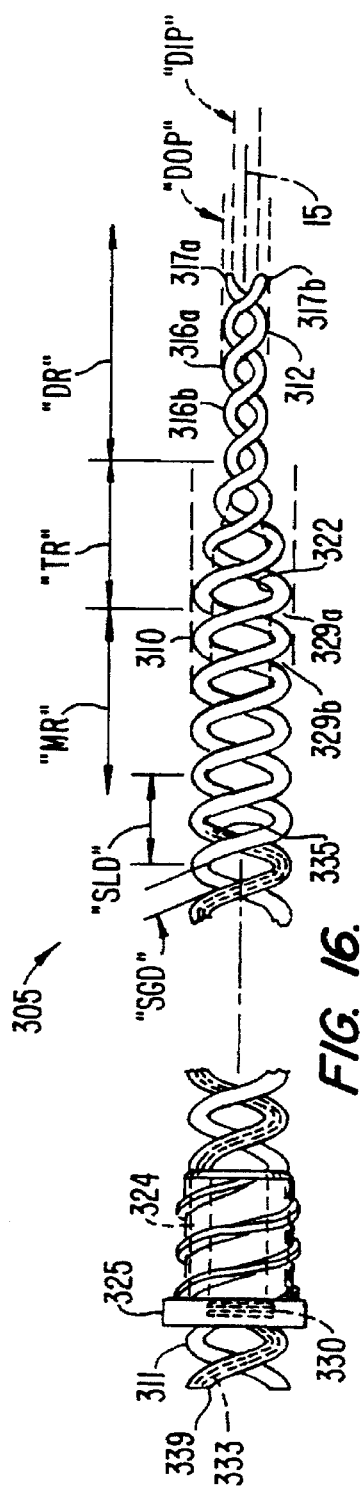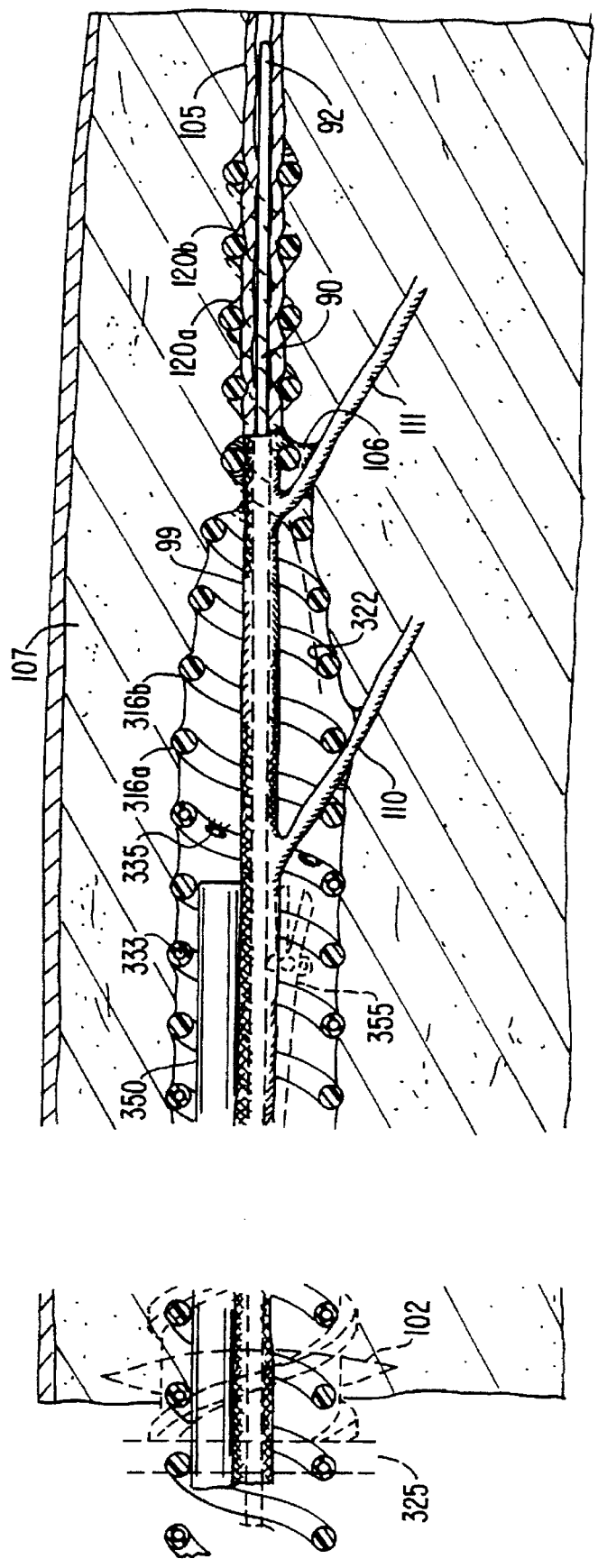
FIG. 16.
FIG. 17C.

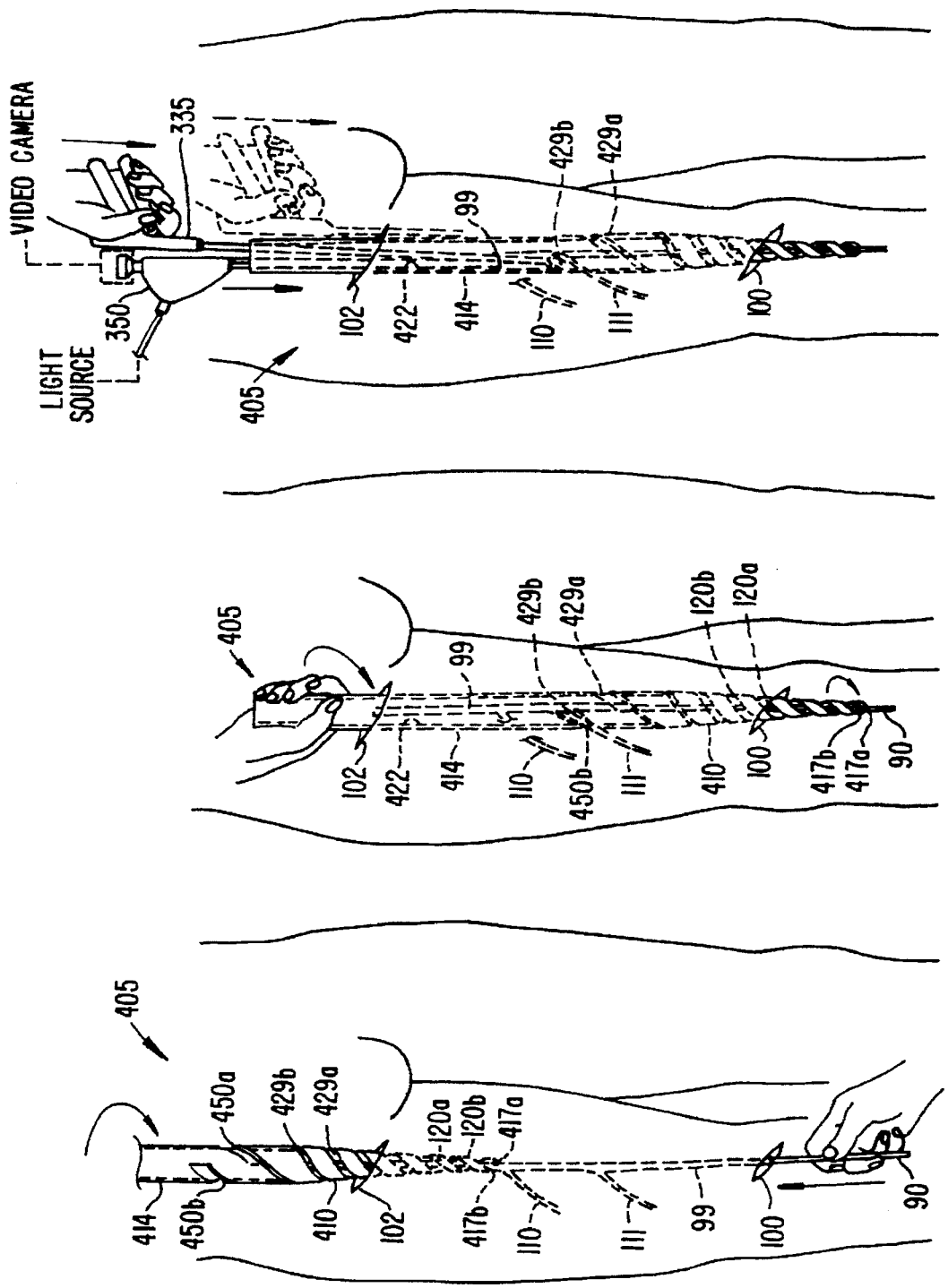

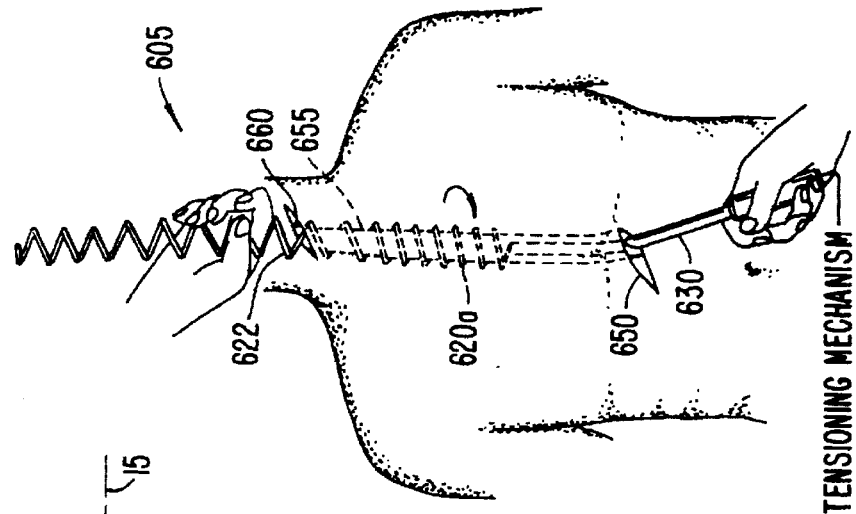
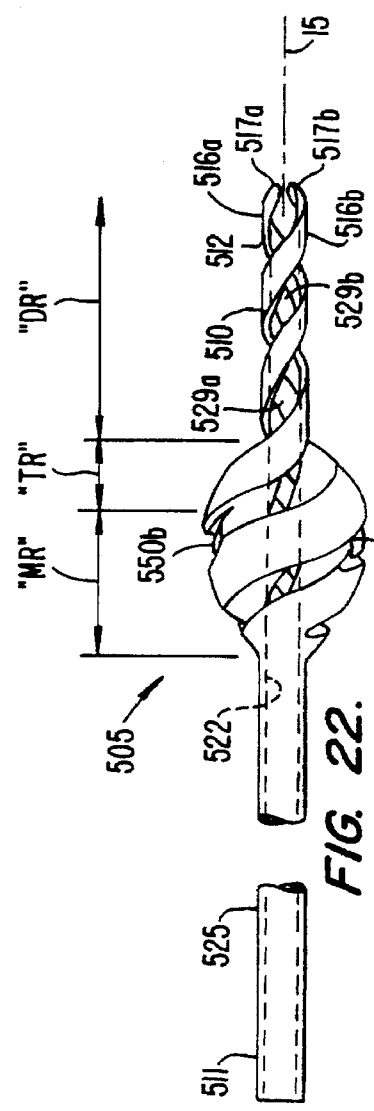
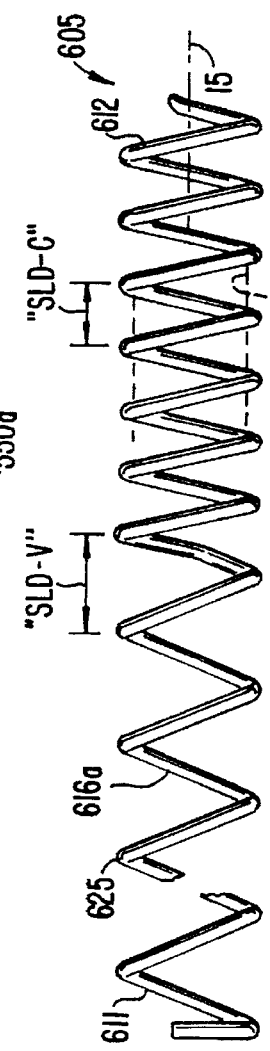
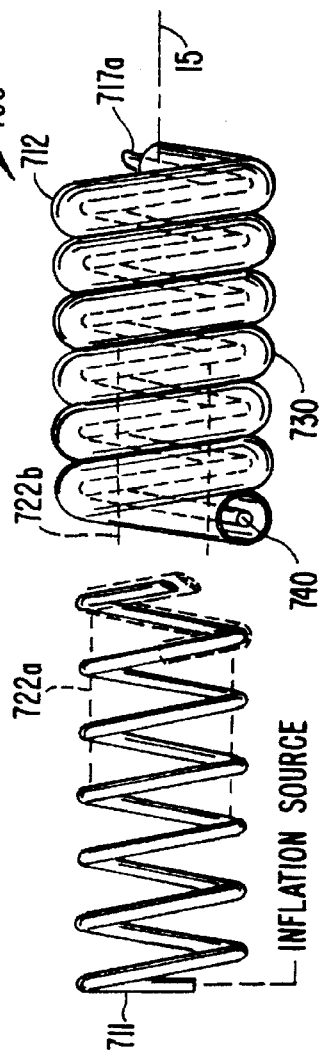

ANTEROGRADE/RETROGRADE SPIRAL DISSECTOR AND METHOD OF USE IN VEIN GRAFTING

CROSS-REFERENCE TO RELATED APPLICATIONS

This application is related to co-pending and commonly invented U.S. patent application Ser. No. 08/334,656, docket no. M-3093 U.S., filed Nov. 4, 1994, now abandoned, which is incorporated herein by reference. This application also is related to the following co-pending and commonly invented U.S. patent applications, all of which are incorporated hereinby reference: Ser. No. 08/287,580, docket no. M-2793 U.S., filed Aug. 9, 1994; Ser. No. 08/316,290, docket no. M-2890-1P U.S., filed Sep. 30, 1994; Ser. No. 08/352,335, docket no. M-3117 U.S., filed Dec. 8, 1994, still pending.

BACKGROUND OF THE INVENTION

1. Field of the Invention

This invention relates to surgical instrumentation and more particularly to instruments and methods for dissecting connective tissues around a vein for grafting purposes in a minimally invasive surgery.

2. Description of Prior Art

In a conventional vein-graft procedure, for example to dissect connective tissues around a saphenous vein and branch veins, an open form of surgery is utilized which is time-consuming and typically results in a lengthy disfiguring incision.

SUMMARY OF THE INVENTION

The anterograde and retrograde spiral dissectors of the present invention are adapted for dissecting connective tissues around the surface of a blood vessel (or other anatomic structure) to facilitate a vein graft or other surgical procedure. Such spiral dissectors are described herein with reference to exemplary methods of dissecting around a saphenous vein in preparation for an in-situ saphenous vein bypass of a patient's tibial artery and in harvesting a saphenous vein for grafting elsewhere in the body.

In general, an antero/retrograde spiral dissector comprises one or more elongate spiral members, each having a blunt distal tip adapted for helical advancement in a plane around the surface of a vein. Anterograde helical advancement of the spiral members bluntly dissect small diameter "guide paths" in connective tissues with little resistance to penetration. With the spiral dissector thus helically engaged, the instrument drives itself anterograde (distally) upon rotation of a proximal handle. The spiral dissector includes a "path-expanding" means associated with either a distal, medial or proximal region of each spiral member, by which is meant a path-expanding structure is adapted for anterograde or retrograde travel along the dissected "guide paths" to further expand the dimensions of the guide paths thereby to dissect connective tissues in a 360° plane around the vein.

In performing an exemplary method of a retrograde dissection around a saphenous vein and branch veins, the surgeon makes a small incision near the patient's knee, performs a renotomy and advances a guide probe (or stent) though the vein to the region of the patient's groin. The surgeon makes a second incision in the groin to expose the vein. The surgeon then pushes the distal tips of the spiral members into the connective tissue plane around the vein and advances the instrument helically and anterograde (distally). The distal tips of the spiral members are angled radially inward to press against the guide stent within the vein. The distal tips of the spiral members are somewhat flexible and will deflect and advance around branch veins. Thus, helical and anterograde advancement of the spiral members bluntly dissect small diameter spiral "guide paths" around the vein between the patient's groin and knee.

The surgeon then introduces an inflation medium into inflatable sleeves (a path-expanding means) at a distal tip of each spiral member. Thereafter, the surgeon helically and retrograde (proximally) withdraws the instrument. The retrograde (reverse) movement of each inflatable sleeve thereby dissects outwardly along each dissected "guide path" thus expanding such paths until they intersect to dissect connective tissues in a 360° plane around the vein along lines of least resistance to provide a relatively blood-free plane. Each inflated sleeve has a sufficient transverse dimension to abut an adjacent inflated sleeve, yet branch veins are left undisturbed as the sleeves deform to pass around such branch veins.

Upon removal of the spiral dissector from the groin incision, the branch veins may be transected a distance outward from the saphenous vein by utilizing the endoscopic instrument disclosed in application Ser. No. 08/316,290 docket no. M-2890-1P U.S., filed Sep. 30, 1994 referenced above.

In an "anterograde" embodiment of a spiral dissector, spiral members are advanced helically and anterograde around a vein to dissect spiral "guide paths" as described above. Thereafter, a "path-expanding" means is moved "anterograde" (forward) along the guide paths thus expanding such paths to dissect connective tissues in a 360° plane around the vein. The "path-expanding" means may be an inflatable sleeve or a structure with flexible bows having an increased transverse dimension compared to the spiral member. Also, the "path-expanding" means may comprise a spiral assembly having an increasing radial dimension in the proximal direction to lift muscle tissue away from the vein. Also, the "path-expanding" means may comprise a spiral member having a variable spiral lead (pitch) associated with a medial or proximal portion of the spiral member. Such a variable spiral lead causes longitudinal stretching and blunt dissection along a "guide path" due to the mis-match between the spiral of the path and the instrument.

Another embodiment of an "anterograde" spiral dissector includes an incising structure for transecting branch veins as the instrument is moved helically and anterograde. Such branch veins are transected radially outward from the main vein by a blade fixed in the spiral gap between adjacent spiral members.

Another embodiment of an "anterograde" spiral dissector is adapted for temporary or permanent placement around a blood vessel as an extraluminal "constraint" for constraining a transverse dimension of a blood vessel or other anatomic structure, e.g.; to reinforce a vessel wall in a region of an aneurysm. A distal "constraint" section of a spiral element may be made of biocompatible or biosorbable material and placed around a blood vessel in an anterograde blunt dissection. Thereafter, a proximal portion of the instrument may be detached from the distal "constraint" section leaving the "constraint" in place around a portion of the blood vessel. The method of placing such a "constraint" may include the insufflation of the plane around the blood vessel to allow endoscopic viewing of the placement.

In general, the present invention advantageously provides an instrument and method that bluntly dissects connective tissues in a 360° plane surrounding an anatomic structure.

Also provided is an instrument and method in which such a 360° dissection around a vein may be accomplished through a minimally invasive incision rather than in an open surgery.

The present invention advantageously provides an instrument and method that utilizes spiral elements to bluntly dissect "anterograde" spiral guide paths in a 360° plane around an anatomic structure requiring little application of advancing forces. Also provided is an instrument and method that utilizes such a guide path to direct the anterograde of retrograde travel of a path-expanding structure thereby to bluntly dissect connective tissues in a 360° plane around an anatomic structure.

The present invention advantageously provides a path-expanding structure for expanding a guide path comprising an inflatable sleeve for bluntly dissecting connective tissues along lines of least resistance to create a relatively blood-free plane.

Also provided is a path-expanding structure comprising a resilient structure having flexible bows. Also provided is a path-expanding means comprising an increase in a radial dimension of an assembly of probe members for radially stretching and dissecting connective tissues away from a vein. Also provided is a path-expanding means for expanding a guide path comprising a variable spiral lead (pitch) associated with spiral members for stretching and dissecting connective tissues in a generally longitudinal direction along a vein due to a mis-match between a spiral path and a portion of a spiral member.

Also provided is an instrument and method that utilizes an intraluminal guide or stent around which spiral elements may advance helically thus insuring that the spiral elements dissect in a suitable plane in a 360° closely around a surface of an anatomic structure.

Also provided is an instrument and method in which a plurality of flexible tips associated with each spiral probe member will deflect around branch veins of a main vein being dissected. Also provided is an instrument and method in which a spiral gap between adjacent spiral probe members includes an incising structure for transecting branch veins of a blood vessel captured in such a spiral gap.

Also advantageously provided is an instrument and method in which an endoscope and accessory instruments may be introduced into an axial bore defined by said spiral members for viewing treating an anatomic structure. Also provided is an instrument which is made of transparent materials to allow viewing therethrough with an endoscope disposed within an axial bore. Also provided is a method allowing for accessory dissecting instruments to be introduced into an interface between the instrument and surrounding tissue to dissect or ligate branch veins.

Also provided is an instrument and method that provides for contemporaneous or subsequent insufflation of a plane dissected by a spiral dissector for facilitating an endoscopic surgical procedure.

Also provided is spiral element comprising an extraluminal constraint and method for temporary or permanent placement of the spiral element around a blood vessel for constraining a transverse dimension of the blood vessel or other anatomic structure. Also provided is spiral constraint made of biocompatible or biosorbable material for placement around a blood vessel in an anterograde blunt dissection.

The present invention provides an instrument that is inexpensive and may be disposable. Additional advantages and features of the present invention appear in the following description.

DESCRIPTION OF THE DRAWINGS

FIG. 1 is a side view of a Type "A" spiral dissector adapted for a retrograde dissection method in accordance with the present invention showing distal inflatable sleeves in a contracted state.

FIG. 2 is an enlarged longitudinal sectional view of a portion of the instrument of FIG. 1 taken along line 2—2 of FIG. 1.

FIG. 3 is an enlarged side view of a distal portion of the instrument of FIG. 1 taken along line 3—3 of FIG. 1 with inflatable sleeves in an expanded state.

FIG. 4 is an end view of the inflatable sleeves of FIG. 3 taken along line 4—4 of FIG. 3.

FIGS. 5A–5B are perspective views of an alternative path-expanding structure of a spiral dissector in contracted and expanded states.

FIG. 6 is a perspective view of an alternative path-expanding structure in an expanded state.

FIG. 7 is a side view of an intraluminal guide stent (or stent) used in conjunction with the spiral dissector of FIG. 1.

FIGS. 8A–8D are a sequence of cartoons and axionometric views showing the manner in which the instrument of FIG. 1 is utilized to perform a retrograde dissection method of the present invention.

FIG. 9 is a sectional view showing a method of the present invention taken along line 9—9 of FIG. 8D.

FIG. 14 is an end elevational view of the inflatable sleeves of FIG. 3 taken along line 4—4 of FIG. 3.

FIG. 16 is a side view of a Type "C" spiral dissector adapted for an anterograde dissection method in accordance with the present invention.

FIGS. 21A–21C are cartoons showing the manner in which the instrument of FIG. 18 is utilized to perform an anterograde dissection method of the present invention.

FIG. 22 is a side view of a second embodiment of a Type "D" spiral dissector similar to the instrument of FIG. 18.

FIG. 23 is a side view of a Type "E" spiral dissector adapted for an anterograde dissection method in accordance with the present invention.

FIG. 24 is a cartoon showing the manner in which the instrument of FIG. 23 is utilized to perform an anterograde dissection method of the present invention.

FIG. 25 is a side view of a Type "F" spiral dissector of the present invention.

DESCRIPTION OF PREFERRED EMBODIMENTS OF THE INVENTION

Figure 10:
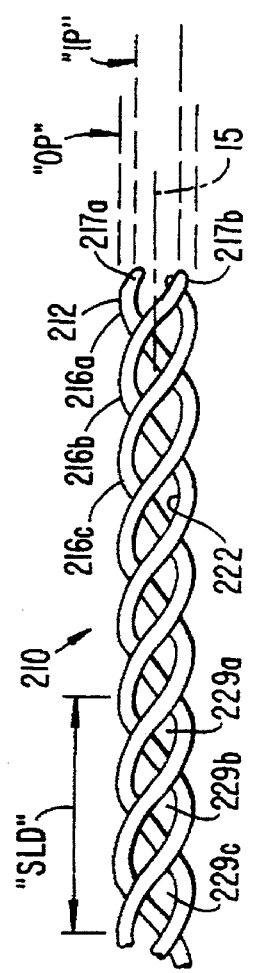
FIG. 10 is a side view of a Type "B" spiral dissector adapted for an anterograde dissection method in accordance with the present invention.

1. Type "A" Retrograde Spiral Dissector. By way of example, FIGS. 1–4 illustrate "retrograde" spiral dissector 5 adapted for dissecting connective tissues surrounding a saphenous vein and comprises elongate spiral assembly 10 with proximal and distal ends, 11 and 12, extending along axis 15. Spiral assembly 10 is made up of one or more spiral probe members and is shown with three probe members 16a, 16b and 16c. It should be appreciated that a spiral dissector preferably has from one to six spiral probes (not limiting) but any number of spiral probes may be within the scope of the present invention. The distal tips, 17a–17c, of the probe members are blunt or rounded. Each probe is made of any suitable material and is preferably a slightly flexible medical grade plastic. The proximal ends of each probe member 16a–16c are fixed in plastic handle 18.

Spiral assembly 10 for a saphenous vein procedure has an cylindrical-shaped outer periphery "OP" having a diameter of approximately 10 mm. to 15 mm. with a overall length of about 400 mm. Each probe member 16a–16c has a diameter ranging from 1 mm. to 5 mm. Referring to FIGS. 1–2, bore 22 along axis 15 is defined by the inner surfaces of the probe members 16a–16c and may be described as the instrument is inner periphery "IP" for accommodating a saphenous vein and has a diameter ranging from 5 mm. to 7 mm. (all dimensions not limiting). As shown in FIGS. 2–3, the distal most tips 17a–17c of probe members 16a–16c, respectively, are angled slightly inward toward axis 15 for reasons explained below.

Each spiral member defines a spiral lead dimension "SLD" as shown in FIG. 1 which may range from 15 mm. to 50 mm. (not limiting). Spiral lead dimension "SLD" may be defined as the axial travel resulting from an angular movement of 360° of a line extending from axis 15 outwardly as the line passes through a helix around axis 15, and as such, the "SLD" generally is equal to the axial travel of spiral dissector 5 in connective tissues around a vein through 360° rotation.

As shown in FIGS. 1–2, each spiral probe member further defines spiral gaps 29a–29c between adjacent convolutions of the probe members. Each such spiral gap defines a spiral gap dimension "SGD" between as shown in FIG. 1 which generally is constant and which may range from 3 mm. to 10 mm. (not limiting).

Referring to FIGS. 1–2, a path-expanding means for bluntly dissecting and expanding a path in connective tissues is provided and comprises inflatable sleeves 30a–a30c having inflation chambers, 33a–33c respectively, carried at the distal end of each spiral probe member 16a–16c. The inflatable sleeves are made of distensible or non-distensible material and are preferably an elastomeric tubular material such as latex. The ends of each sleeve 30a–30c are sealably fixed to each probe member by adhesives or other suitable means thus providing inflation chambers 33a–33c that are fluid-tight.

Inflation means are provided for inflating sleeves 30a–30c around probe members 16a–16c with an inflation medium, preferably saline solution, $CO_2$ gas or another gas. Referring to FIGS. 1–3, inflation lumens 40a–40c within each probe member 16a–16c communicate with respective ports 44a–44c in fitting 45 within handle 18. Thus, each inflatable sleeve separately communicates with an inflation source to insure expansion of each sleeve at a desired pressure level ranging from 2 to 50 psi (not limiting). Fitting 45 may be connected to push-type connector 49 that communicates with a conventional inflation source, for example a syringe containing an inflation medium. As shown in FIG. 3, lumens 40a–40c communicate with inflation chambers 33a–33c through apertures 63a–63c shown in phantom view (aperture 63c not visible).

Of particular interest to the present invention, referring to FIG. 3, the preferred dimensions of an inflatable sleeve for a saphenous vein include axial dimension "AD" ranging from 15 mm. to 25 mm. (not limiting) but the sleeve may be longer an be within the scope of the present invention as described below. A preferred (expanded-state)transverse dimension "TD" as shown in FIG. 4 ranges from 5 mm. to 10 mm. and is generally equal to or greater than the spiral gap dimension "SGD" thereby to press against adjacent expanded-state sleeves for reasons explained below.

It should be appreciated that a pulse mechanism may be provided for causing the volume of an inflation medium in inflation chambers 33a–33c to pulse in intervals to facilitate a blunt dissection of connective tissues as described in co-pending and commonly invented U.S. patent application Ser. No. 08/334,656, docket no. M-3093 U.S., filed Nov. 4, 1994 referenced above.

FIGS. 5A–5B depict an alternative embodiment of path-expanding means and comprises expandable bow-type member 70 that is coupled to a distal end of a spiral probe. In FIG. 5A, bow-type member 70 is shown in a repose (contracted) state with two flexible bows, 72a and 72b, and is made of resilient plastic. FIG. 5B shows bow-type member 70 in a tensioned (expanded) state adapted for a retrograde dissection. Bow-type member 70 is moved between the contracted and expanded states by flexible cable 73 pulled proximally in a lumen within a probe member. An elastomeric sleeve 75 (phantom view) may encase bow-type member 70. FIG. 6 depicts an alternative bow-type member 80 with three flexible plastic bows.

FIG. 7 depicts intraluminal stent or guide 90 made of somewhat flexible plastic (e.g., Delrin®). For a saphenous vein dissection, probe 90 has a diameter ranging from 1 mm. to 3 mm. with proximal end 91 and distal blunt tip 92.

2. Operation of Type "A" Retrograde Spiral Dissector. The use of Type "A" retrograde spiral dissector 5 of FIG. 1 in performing a method of the present invention now may be described briefly in the dissection of connective tissues around saphenous vein 99 in preparation for an in-situ graft of a tibial artery as shown in cartoons (FIGS. 8A–8B), axionometric views (FIGS. 8C–8D) and a sectional view (FIG. 9).

Referring to FIG. 5A, the surgeon makes incision 100 near the patient's knee and exposes saphenous vein 99. The surgeon performs a venotomy and advances guide stent 90 though the lumen of vein 99 to the region of the patient's groin. The surgeon makes groin incision 102, exposes upper portion 103 of the vein and may lift the vein with tape 104.

The surgeon then pushes distal tips 17a–17c of spiral members 16a–16c into plane 105 comprising connective tissues 106 between vein 99 and surrounding muscles layers 107 (see FIGS. 8C–8D and 9). The surgeon then advances the instrument helically and anterograde (distally) with vein 99 accommodated within bore 22. Since probe members 16a–16c are somewhat flexible, the surgeon may substantially bend spiral assembly 10 to introduce distal tips 17a–17c around the vein. As shown in FIG. 8C, when spiral assembly 10 is advanced into plane 105 around the vein, the probe members 16a–16c will tend advance tightly around the vein because tips 17a–17c are angled inward toward axis 15 (see FIGS. 3–4). Also, the probe members will not diverge away from plane 105 around vein 99 because each probe member is helically engaged around guide stent 90 within the lumen of vein 99.

Referring to FIG. 8C, it can be seen that any distal tip, 17a–17c, that hits a branch vein, 110 or 111, will deflect and advance around such a branch vein. The spiral probe members 16a–16 thus dissect small-diameter "guide paths" 120a–120c around vein 99 as shown in phantom views in FIGS. 8C–8D. The surgeon advances dissector 5 anterograde through the patient's thigh until distal tips 17a–17c are visible in incision 100 near the patient's knee. Thereafter, the surgeon introduces an inflation medium into inflation chambers 33a–33c of each inflatable sleeve 30a–30c (e.g., with a syringe) and then withdraws dissector 5 helically and retrograde (proximally).

Of particular interest to the present invention, the retrograde or reverse movement of each inflatable sleeve 30a–30c is guided by each spiral probe 16a–16c still disposed within guide paths 120a–120c (see FIG. 8D). Thus, each expanded sleeve bluntly dissects plane 105 outwardly from each guide path resulting in the dissection of plane 105 in 360° around vein 99. All branch veins, 110 and 111, are left undisturbed by such retrograde movement as the inflated sleeves deform and pass around the branch veins as shown in FIG. 9. It can be seen that connective tissues 106 between branch vein 110 and muscles 107 are dissected a distance radial outward from vein 99 by a distance generally equal to transverse dimension "TD" of an inflatable sleeve, albeit compressed with plane 105 (see FIG. 9).

To further prepare vein 99 for an in-situ bypass, it is necessary to transect branch veins, 110 and 111, preferably at a distance away from vein 99. The transection or ligation of branch veins may be accomplished under endoscopic vision by utilizing the "enveloping sleeve" and method disclosed in co-pending U.S. patent application Ser. No. 08/316,290 docket no. M-2890-1P U.S., filed Sep. 30, 1994 referenced above. The section of saphenous vein 99 below the patient's knee may be spirally dissected away from surrounding muscles by repeating the above-described procedure, this time between another incision below the calf (not shown) and incision 100. The valves within vein 99 may be incised with a Hall valvulotome of known construction inserted through a cut end of the vein. Thereafter, a transected proximal end of vein 99 in the groin may be grafted onto a proximal portion of a defective artery (not shown) and likewise a transected distal end of vein 99 may be grafted to a distal portion of the artery (not shown) to complete an in-situ reversed flow saphenous vein bypass of the artery in a minimally invasive procedure.

It should be appreciated that utilizing spiral dissector 5 to dissect only small diameter guide paths 120a–120c around vein 99, followed by helical withdrawal of the instrument without expanding the inflation sleeves will facilitate the use of the "enveloping sleeve" and method disclosed in co-pending U.S. patent application Ser. No. 08/316,290 for accomplishing a vein graft.

It should be appreciated that a dissection of a saphenous vein, other blood vessel or other anatomic structure may be accomplished either with or without use of an intraluminal guide stent and be within the scope of the present invention. Also, guide stent and spiral dissector may be advanced from the same direction or opposite directions in relation to an anatomic structure and be within the scope of the present invention. Herein, intraluminal probe 90 is advanced upward from the knee to facilitate passage of the probe through valves within vein 99.

3. Type "B" Anterograde Spiral Dissector. FIG. 10 illustrates a Type "B" spiral dissector 205 adapted for "anterograde" dissection around a saphenous vein in which like reference numbers refer to elements common to the previously described embodiment and its method of use. Spiral dissector 205 has elongate spiral assembly 210 with proximal and distal ends, 211 and 212, extending along axis 15. Spiral assembly 210 is made up of a plurality of spiral probe members, here shown with three probe members 216a, 216b and 216c. The distal tips, 217a–217c, of the probe members are blunt and each probe is made of any suitable material, e.g., a slightly flexible medical grade plastic.

Figure 12:
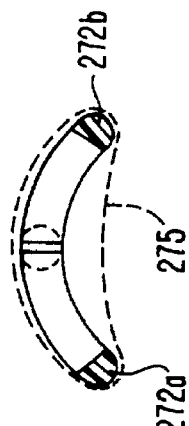
FIG. 12 is a transverse sectional view of the handle of FIG. 11 taken along line 12—12 of FIG. 11.
Figure 11:
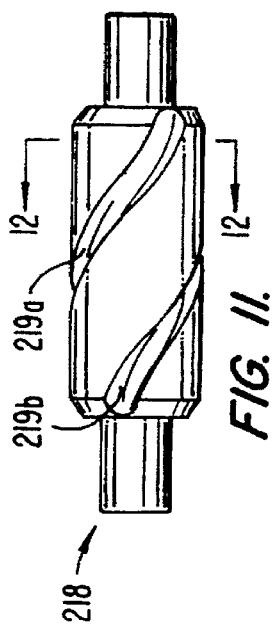
FIG. 11 is an enlarged side of a demountable handle member of the instrument of FIG. 10.

As shown in FIGS. 10 and 11, a proximal region of each probe member 216a–216c is detachably coupled to plastic handle 218 having spiral grooves 219a–219c impressed therein. FIG. 12 depicts a sectional view of handle 218 and each groove 219a–219c is dimensioned for a detachable press fit as the flexible probe members are bent inward and outward into the grooves.

Spiral assembly 210 for a saphenous vein procedure has a cylindrical outer periphery "OP" that is approximately 7 mm. to 25 mm. in diameter with a overall length of about 400 mm. Each probe member 216a–216c has a diameter ranging from 1 mm. to 4 mm. providing bore 222 along axis 15 having an inner periphery "IP" ranging in diameter from 5 mm. to 7 mm. (all dimensions not limiting).

Spiral probe members 216a–216c have a constant spiral lead and define spiral lead dimension "SLD" as described in a Type "A" dissector above. The spiral probe members define spiral gaps 229a–229c between adjacent convolutions having a gap dimension "SGD" (see FIG. 10) that is constant and ranges from 3 mm. to 10 mm. (not limiting).

Figure 13:
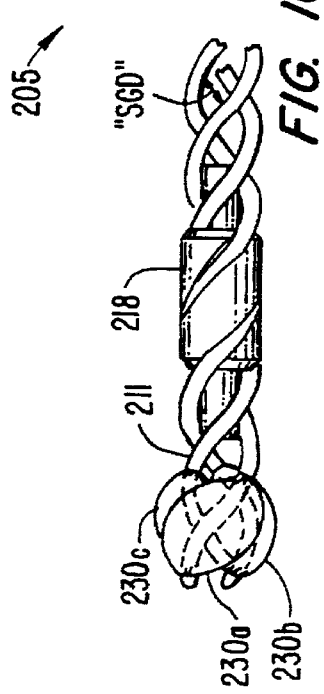
FIG. 13 is an enlarged side view of a proximal portion of the instrument of FIG. 10 taken along line 13—13 of FIG. 10.

Referring to FIGS. 10 and 13, path-expanding means are provided to bluntly dissect connective tissues and comprise expansion sleeves 230a–230c each having a sealed expansion chamber 233a–233c. This Type "B" spiral dissector carries each expansion sleeve at a proximal end of each spiral probe member 216a–216c for an anterograde dissection.

Figure 14A:
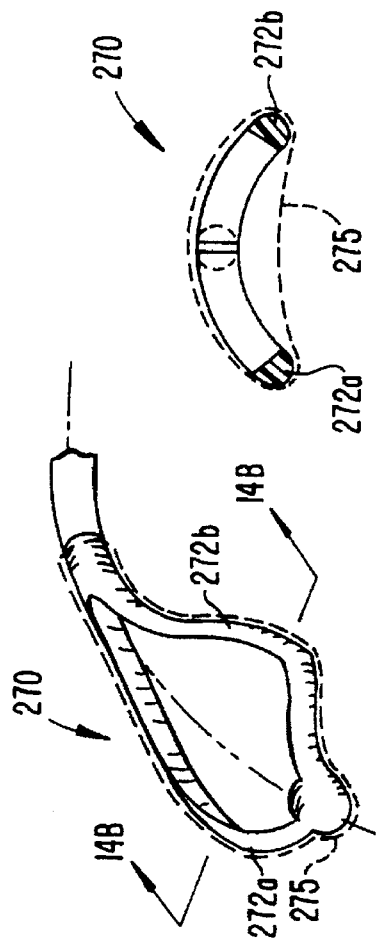
FIGS. 14A–14B are perspective and sectional views of an alternative path-expanding portion a spiral dissector.
Figure 14B:
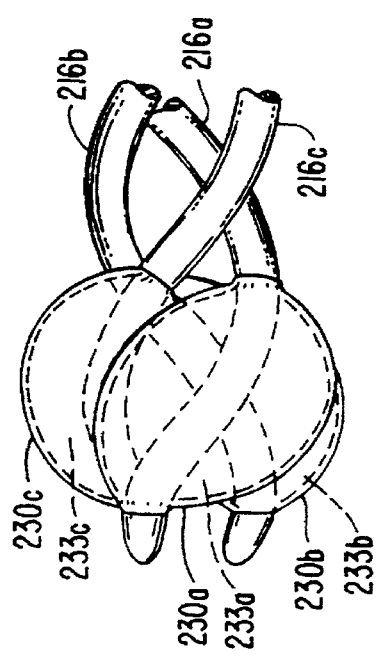

FIGS. 14A–14B depict an alternative path-expanding means and comprise an expandable bow-type member 270 that is coupled to a proximal end of a probe member. In FIG. 14A, bow-type member 270 is shown in with two flexible bows, 272a and 272b, and is made of resilient plastic. An elastomeric sleeve 275 (phantom view) may encase bow-type member 270. FIG. 14B shows a transverse section of bow-type structure 270 and illustrates a curved sectional shape for fitting around the circumference of blood vessel or other anatomic structure.

4. Operation of Type "B" Anterograde Spiral Dissector. The use of Type "B" anterograde dissector 205 of FIG. 2 in performing a method of the invention is described briefly in the dissection of a greater saphenous vein as shown in the cartoons of FIGS. 15A–15B.

Figure 15A:
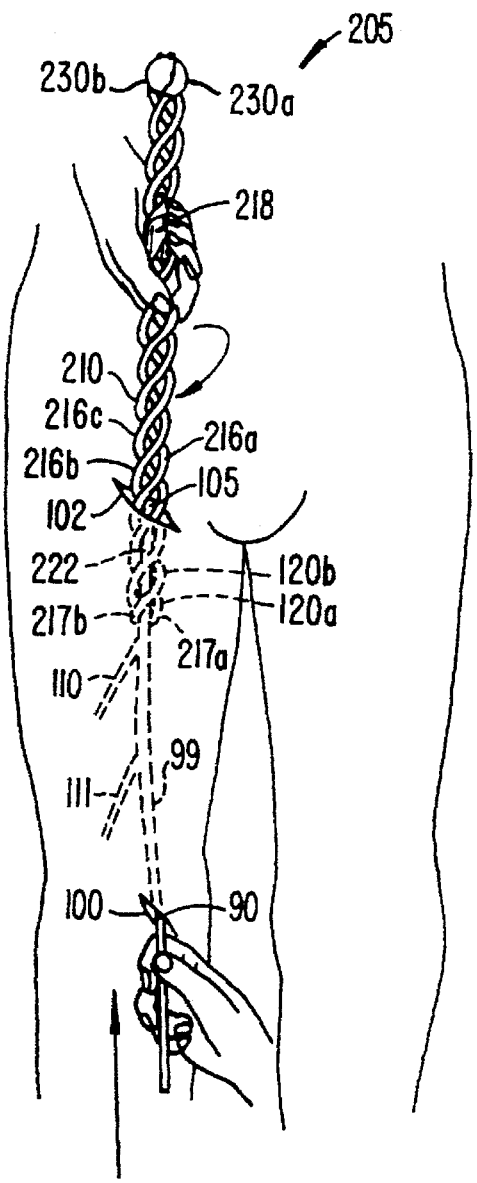
FIGS. 15A–15B are cartoons showing the manner in which the instrument of FIG. 10 is utilized to perform an anterograde dissection method of the present invention.
Figure 15B:
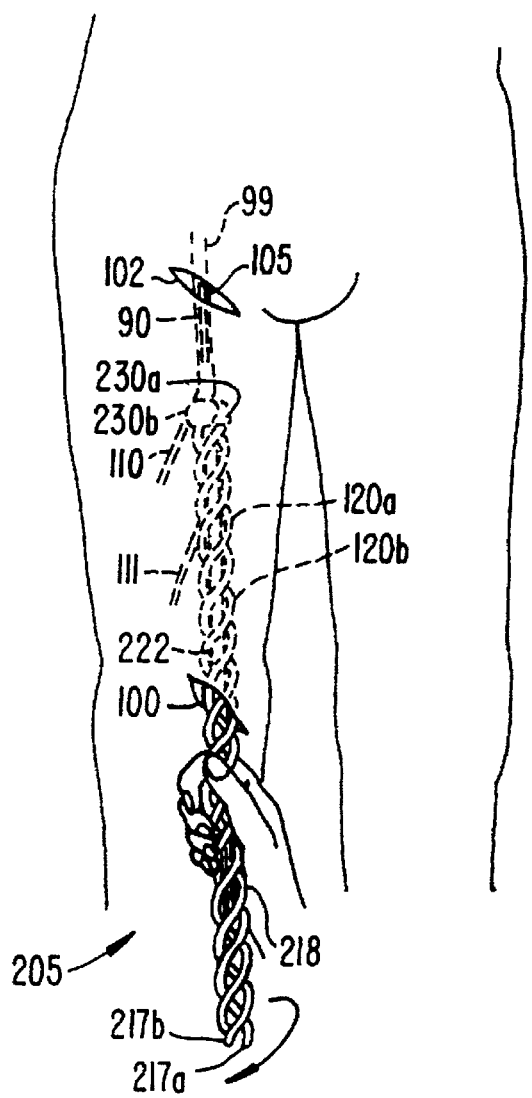

Referring to FIG. 15A, the surgeon makes incisions 100 and 102 in the patient's leg and advances guide stent 90 though the lumen of saphenous vein 99 as described previously. The surgeon then introduces distal tips 217a–217c of spiral members 216a–216c into plane 105 around vein 99 and advances the instrument helically and anterograde (distally). The vein 99 is accommodated within bore 222 within spiral assembly 210. As shown in FIG. 15B, the surgeon advances the instrument until distal tips 217a–217c are exposed outside incision 100 near the patient's knee. Still referring to FIG. 15B, the surgeon de-mounts handle member 218 from the proximal section of spiral assembly and mounts the handle in distal section of the spiral assembly thus maintaining the spiral members as a unit. The surgeon then helically and anterograde advances dissector 205 outwardly from knee incision 100.

Of particular interest to the present invention, the anterograde movement of each expansion sleeve 230a–230c is guided along each dissected guide paths 120a–120c. Each expanded sleeve thereby bluntly dissects connective tissues around each guide path until plane 105 is dissected in 360° around vein 99. Branch veins, 110 and 111, are left undisturbed by such anterograde movement as the expansion sleeves deform and pass around the branch veins (cf. FIG. 8D except for the direction of travel). The remainder of the dissection procedure follows the method described above in using a Type "A" spiral dissector, for example utilizing the enveloping sleeve and method disclosed in co-pending U.S. patent application Ser. No. 08/316,290, docket no. M-2890-1P U.S.

5. Type "C" Spiral Dissector. FIG. 16 illustrates a Type "C" spiral dissector 305 adapted for "anterograde" dissection of connective tissues in a plane around a saphenous vein. Spiral dissector 305 has elongate spiral assembly 310 with proximal and distal ends, 311 and 312, extending along axis 15. Spiral assembly 310 may comprise from one to six or more spiral probe members, and is shown in FIG. 16 with two probe members, 316a and 316b having blunt distal tips, 317a–317b.

Referring to FIG. 16, spiral assembly 310 for a saphenous vein dissection includes a distal region "DR" that is cylindrical-shaped with an distal outer periphery "DOP" ranging in diameter from approximately 7 mm. to 15 mm. The spiral assembly has tapered region "TR" that transitions to medial region "MR" with a taper angle relative to axis 15 ranging from 10° to 45° or more. The medial outer "MR" has an outer periphery that ranges in diameter from approximately 20 mm. to 40 mm. Each probe member 316a–316b has a diameter ranging from 1 mm. to 4 mm. (dimensions not limiting).

Referring to FIG. 16, bore 322 along axis 15 is defined by the inner surfaces of the probe members 316a–316b and defines the instrument's distal inner periphery "DIP" ranging from 3 mm. to 6 mm. and adapted to fit closely around a saphenous vein having guide stent within its lumen. Bore 322 has an enlarged diameter in medial region "MR" ranging from 25 mm. to 35 mm. adapted for accommodating accessory instruments as described hereinbelow.

Spiral probe members 316a–316b generally exhibit a constant spiral lead defining a spiral lead dimension "SLD" as well as spiral gaps 329a–329c having a spiral gap dimension or "SGD" (see FIG. 16) ranging from 3 mm. to 10 mm. (not limiting).

As shown in FIG. 16, the proximal and medial regions of each probe member 316a–316b are slidably mounted in helical channels in collar 324 that freely rotates in skin seal 325. Skin seal is depicted with double-flight helical threads for providing a fluid tight seal in a skin incision. Collar 324 is further provided with a centrally mounted instrument seal 330 of the type disclosed in copending and commonly invented U.S. patent application Ser. No. 08/352,335, docket no. M-3117 U.S., filed Dec. 8, 1994 referenced above.

Optional insufflation means are provided for insufflating a dissected plane around a saphenous vein and includes interior lumen 333 within probe member 316a communicating between an external insufflation source and one or more apertures 335 in a medial region of probe member 316a. A flexible insufflation hose (not shown) may be connected to Luer-type fitting 339 molded into a proximal end of spiral probe member 316a (see FIG. 16).

Figure 17A:
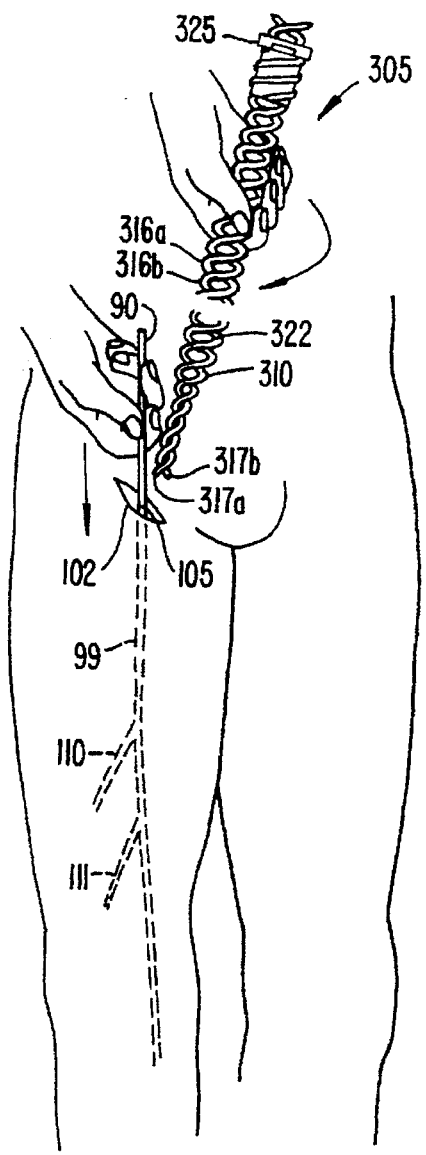
FIGS. 17–17C are cartoons and a sectional view showing the manner in which the instrument of FIG. 16 is utilized to perform an anterograde dissection method of the present invention.
Figure 17B:
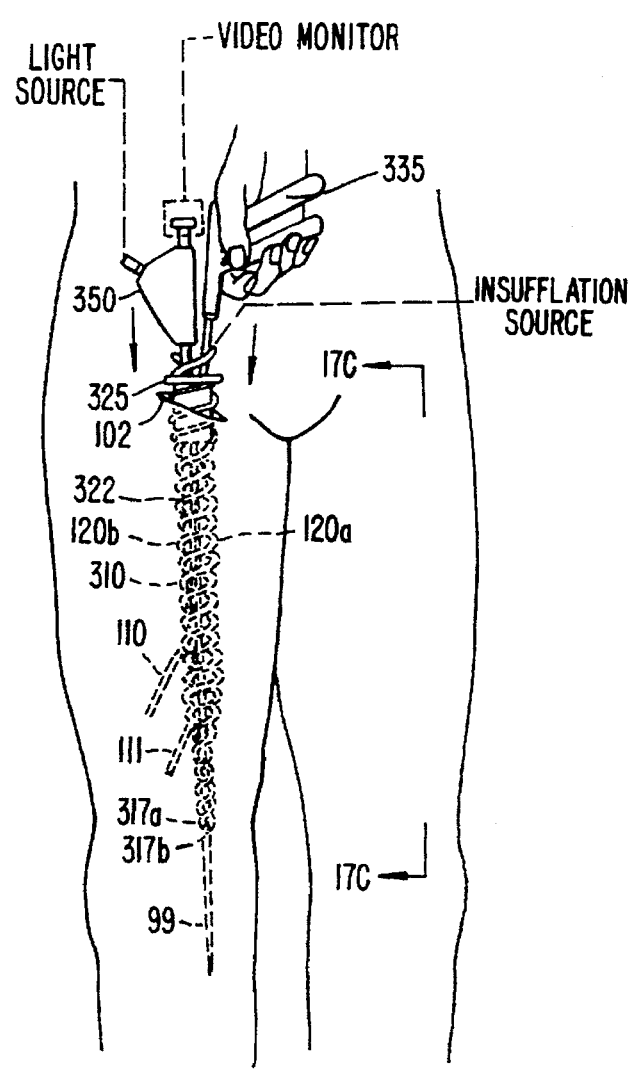

6. Operation of Type "C" Spiral Dissector. The use of spiral dissector 305 of FIG. 16 in performing an anterograde dissection of a vein is illustrated in FIGS. 17A–17C. Referring to FIG. 17A, assume that the surgeon inserts intraluminal guide stent 90 into vein 99 through incision 100. The surgeon introduces distal region "DR" of the spiral dissector 305 into plane 105 around vein 99 and then advances the instrument helically and anterograde as shown in FIG. 17B.

Of particular interest to the present invention, referring to FIG. 17C, spiral dissector 305 bluntly dissects connective tissues 106 in plane 105 along guide paths 120a–120b by driving the increased outer periphery of medial region "MR" of assembly 310 into plane 105. In other words, the path-expanding means comprises the increasing transverse dimension of the tapered region "TR" that lifts muscles 107 away from vein 99. Still, the distal region "DR" having a lesser-dimensioned distal outer periphery "DOP" helically engages connective tissues 106 in plane 105 causing the instrument it to pull itself in an anterograde direction upon rotation.

Referring to FIG. 17C, the surgeon then introduces endoscope 350 through seal 330 into dissected plane 105 to view vein 99 and surrounding tissue. Thereafter, the surgeon introduces an accessory dissecting instrument 355 (e.g., a scissors) alongside endoscope 350 through seal 330 to transect branch vein 110. It should be appreciated that endoscope 350 and accessory instrument 355 are of the type that disclosed in U.S. patent application Ser. No. 08/352,335, docket no. M-3117 U.S., referenced above, having handle members adapted for manipulation side-by-side through in a single "port assembly" in a single incision in the patient's body. The remainder of an in-situ by-pass procedure may be completed as described above with a Type "A" dissector.

It should be appreciated that in insufflation source may be connected to Luer-type fitting 339 of probe member 316a to insufflate plane 105 through interior lumen 333. As can be seen in FIG. 17C, insufflation gases flow through apertures 335 in probe member 316a. It also should be appreciated that spiral dissector 305 may be removed from incision 102 and the dissected plane may thereafter be insufflated to facilitate a surgical procedure such as transecting branch veins using the dual-port cannula assembly and other methods disclosed in U.S. patent application Set. No. 08/352,335, docket no. M-3117 U.S., referenced above.

Figure 18:
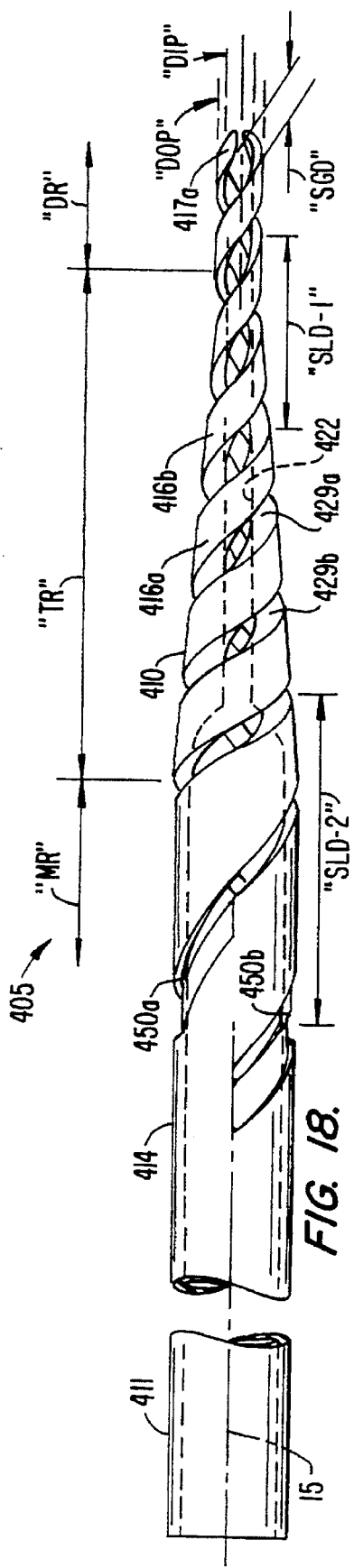
FIG. 18 is a side view of a Type "D" spiral dissector adapted for an anterograde dissection method in accordance with the present invention.

7. Type "D" Anterograde Spiral Dissector. FIG. 18 illustrates a Type "D" spiral dissector 405 adapted for anterograde blunt dissection of connective tissues around a vein. Dissector 405 is a unitary member with proximal and distal ends, 411 and 412, extending along axis 15 and preferably is made of injection-molded transparent medical grade plastic. Spiral portion 410 has a plurality of from two to four spiral elements extending distally from a tubular portion 414 and is shown in FIG. 18 with two spiral elements, 416a and 416b with blunt distal tips, 417a–417b.

Referring to FIG. 18, dissector 405 has a distal region "DR" with a distal outer periphery "DOP" that is cylindrical-shaped with a length ranging from 0 mm. to 50 mm. and a diameter ranging approximately 7 mm. to 15 mm. Tapered region "TR" transitions to medial region "MR" at any angle ranging from 10° to 45° or more. The medial region's outer periphery ranges in diameter from approximately 20 mm. to 40 mm. (all dimensions not limiting).

Figure 19:
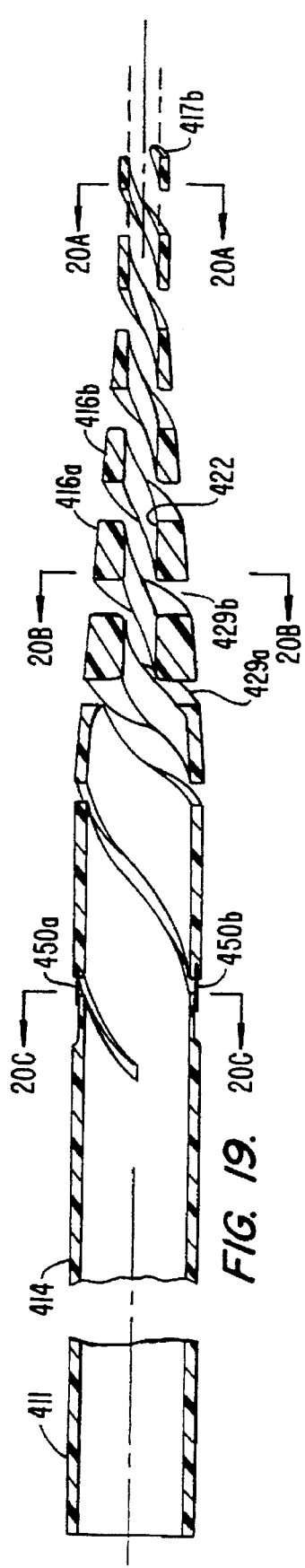
FIG. 19 is a longitudinal sectional view of the instrument of FIG. 18 taken along line 19—19 of FIG. 18.

Referring to FIG. 19, bore 422 along axis 15 is defined by the inner surfaces of probe elements 416a–416b and tubular portion 141 and has a distal inner periphery "DIP" ranging from 3 mm. to 6 mm. to fit closely around a saphenous vein. Bore 422 in the medial region "MR" ranges from 25 mm. to 35 mm. and is adapted for accommodating accessory instruments similar to the previously-described Type "C" dissector.

A path-expanding means is provided for expanding and bluntly dissecting connective tissues along a spiral path and comprises an increased cross-sectional dimension of each spiral element 416a–416b. Such increased cross-sectional dimension is associated with the increased radial dimension of tapered region "TR" as well as spiral gaps 429a–429b having a spiral gap dimension "SGD" that decreases in the proximal direction. Thus, it can be seen that each spiral element 416a–416b has a small cross-section at distal end 412 and such cross-section progressively increases in the proximal direction (cf. FIGS. 19, 20A and 20B).

Figure 20A:
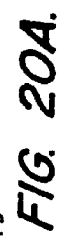
FIGS. 20A–20C are transverse sectional views of the instrument of FIG. 18 taken along lines 20A—20A, 20B—20B, 20C—20C of FIG. 19.
Figure 20B:
Figure 20C:
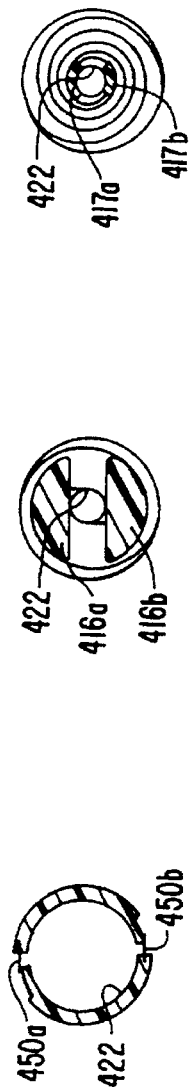

Means are provided for automatically incising branch veins as the instrument is advanced helically and anterograde around a vein. Referring to FIGS. 18, 19 and 20C, it can be seen that an incising blades, 450a and 450b, are fixed in a proximal portion of spiral gaps 429a and 429b. For example, such incising members may be made of flexible stainless steel in thicknesses ranging from .002 to 0.010 similar to razor blade material with a sharp edge. Each blade member, 450a and 450b, is angled across spiral gaps 429a and 429b, respectively and cooperates with grooved portion 452a and 452b in the wall of tubular portion 414. As can be seen in FIGS. 19 and 20A, the distal region "DR" of each spiral element 416a–416b defines a spiral lead dimension "SLD-1" that generally is constant. The medial region "MR" of the instrument is shown having an increased "SLD-2" for reasons explained below.

8. Operation of Type "D" Spiral Dissector. The use of spiral dissector 405 of FIG. 18 in performing a method of the present invention is illustrated in the cartoons of FIGS. 21A–21C. Referring to FIG. 21A, assume that the surgeon inserts intraluminal guide stent 90 into vein 99 through incision 102 and then introduces the distal end 412 of dissector 405 into the plane around vein 99. The surgeon advances the instrument helically and anterograde and tips 417a–417b of spiral members 416a–416b deflect around branch veins and capture the branch veins in either spiral gap, 429a or 429b. As shown in FIG. 21B, the instrument in advanced distally until distal end 412 of spiral portion 410 is near the patient's knee or extends outward through incision 100.

Referring to FIG. 21B, it can be seen that the distal region "DR" of the instrument bluntly dissects connective tissues along spiral paths 120a and 120b in plane 105. Of particular interest to the present invention, the increased cross-section of each spiral element 416a and 416b associated with tapered region "TR" expands such preestablished paths and progressively lifts muscles 107 away from vein 99 until the plane around vein 99 is entirely dissected. Still, the distal region "DR" of assembly 405 helically engages connective tissues in plane 105 causing the instrument to drive itself anterograde (distally) upon rotation.

As can be seen in FIG. 21B, as branch vein 110 or 111 is captured in either spiral gap (429a or 429b) and dissector 405 is advanced anterograde, either incising blade 450a or 450b will contact and cut a branch vein in respective spiral gaps. The increased spiral lead dimension "SLD-2" (see FIG. 18) causes a branch vein to slide along a distal edge of either spiral gap 429a or 429b and thereafter directly into an incising blade.

As shown in FIG. 21B, the surgeon may introduce endoscope 350 into bore 422 and view dissected plane through the transparent walls of the tubular portion 414 of dissector 405. Also, the surgeon may introduce an accessory dissecting instrument 355 (e.g., a scissors) into bore 422 to transect a branch vein or perform other procedures. As shown in phantom view in FIG. 21B, an accessory dissecting instrument also may be introduced into a plane around the exterior of spiral dissector 405 to transect a branch vein or perform other procedures while viewing with endoscope 350 through the transparent walls of the instrument.

FIG. 22 depicts another embodiment of Type "D" spiral dissector 505 with proximal and distal ends, 511 and 512, extending along axis 15 and preferably is made of injection-molded plastic. Spiral portion 510 is depicted with two spiral elements, 516a and 516b and blunt distal tips, 517a–517b. Dissector 505 has a distal region "DR" with a distal outer periphery around bore 522 that is adapted for creating spiral paths around a vein. Dissector 505 differs from the previously-described embodiment in that tapered region "TR" transitions to a short medial region "MR". The proximal portion 525 of dissector 505 has a reduced dimension for ease of penetration through tissue. The medial region "MR" comprises a path-expanding including an increased radial dimension as described above and includes blades 550a and 550b for incising branch veins in spiral gaps 529a and 529b. It should be appreciated that bore 522 may be increased in medial region "MR" although a smaller dimension bore helps insure that branch veins are transected radially outward from axis 15. Spiral dissector 505 is utilized in a manner similar to the cartoons of FIGS. 21A–21B.

9. Type "E" Anterograde Spiral Dissector. By way of example, FIG. 23 illustrates a Type "E" spiral dissector 605 adapted for anterograde blunt dissection of connective tissues around an anatomic structure, e.g., an esophagus. Spiral dissector 605 has proximal and distal ends, 611 and 612, extending along axis 15 and preferably is made of injection-molded medical grade plastic. Dissector 605 is shown with a single spiral member 616a (not limiting) defining bore 622 for dissecting a guide path 620a (see FIG. 24).

A path-expanding means is provided for expanding pre-established guide path 620a and comprises variable spiral lead portion 625 associated with spiral probe member 616a. By variable spiral lead, it is meant that probe member 616a has a distal portion that defines a constant spiral lead dimension "SLD-C". The medial portion of the instrument has a variable spiral lead dimension "SLD-V" wherein probe member 616a varies its lead dimension (see FIG. 23). Alternatively, the variable spiral lead dimension may be increased and decreased rapidly to impart a generally sinuous shape to accomplish the method of the invention as described below.

10. Operation of Type "E" Spiral Dissector. The use of spiral dissector 605 of FIG. 18 in performing a method of the present invention is illustrated in the cartoon of FIG. 24 in a dissection of connective tissues around an esophagus in preparation for an esophagectomy. Referring to FIG. 24, assume that the surgeon inserts an intraluminal retractor or stent 630 of the type disclosed in U.S. patent application Ser. No. 08/287,580, docket no. M-2973 U.S., filed Aug. 9, 1994 through incision 650 in a patient's abdomen. The surgeon then advances distal portion of dissector 605, and more particularly the distal portion of bore 622 around esophagus 655 in neck incision 660. As shown in FIG. 23, the instrument in advanced anterograde until the distal end of dissector 605 appears through incision 650.

It can be seen that the distal region of dissector 605 bluntly dissect path 620a in connective tissues in a plane around esophagus 655. Of particular interest to the present invention, the medial region portion with a variable spiral lead portion 625 will follow the preestablished path 620a at first. Then, rotation of the instrument dissects the weak connective tissues around esophagus 655 because the variable-lead portion 625 and spiral path 620a are mismatched and the connective tissues yield and are thus dissected. Still, the distal region "DR" of dissector 605 helically engages connective tissues in the plane around esophagus 655 allowing the instrument to drive itself anterograde upon rotation.

11. Type "F" Anterograde Spiral Dissector. By way of example, FIG. 25 illustrates a Type "F" spiral dissector 705 adapted for anterograde blunt dissection of connective tissues around an esophagus or other anatomic structure. Spiral dissector 705 has proximal and distal ends, 711 and 712, extending along axis 15. Dissector 705 is shown with a single spiral member 716a (not limiting) for dissecting a guide path 720a. A path-expanding means is provided for expanding pre-established guide path 720a as well as for gripping a resected anatomic structure captured within constricted bore 722b comprising a distensible or non-distensible sleeve 730. Dissector 705 differs from a Type "A" dissector (see FIGS. 1–4) described above principally in that sleeve 730 extends over a lengthy portion of the spiral member.

12. Operation of Type "F" Spiral Dissector. The use of spiral dissector 705 of FIG. 25 in performing a method of the present invention is similar to the cartoon of FIG. 24 in a dissection of connective tissues in a resection of an esophagus. The surgeon inserts an intraluminal retractor or stent 630 of the type disclosed in U.S. patent application Ser. No. 08/287,580, docket no. M-2973 U.S., filed Aug. 9, 1994 into the esophagus. The surgeon then advances dissector 705, and more particularly the axial bore 722a around esophagus 655 thus bluntly dissecting a guide path in connective tissues in a plane around esophagus 655. Thereafter, the surgeon inflates inflatable sleeve 730 along pre-established guide path to dissect connectives in a 360° plane around the esophagus as the adjacent convolutions of the inflated sleeve expand to contact one another. The surgeon then transects the esophagus in the abdominal and neck incisions. With the inflatable sleeve 730 in its expanded state and the axial bore 722b in a constricted state, the resected esophagus is captured between sleeve 730 and intraluminal stent 630. Thereafter, the surgeon may move the instruments axially or rotationaly to further mobilize the esophagus. Then, stent 630 may be withdrawn and dissector 705 may be removed upwardly with the esophagus captured in bore 722b to complete the resection.

Another embodiment of an "anterograde" spiral dissecting device with a single spiral element similar to FIG. 23 but dimensioned for a close fit around a blood vessel may be adapted as a temporary or permanent extraluminal "constraint" for constraining a transverse dimension of the blood vessel. Such a "constraint", when helically advanced around a blood vessel (or other anatomic structure) may be utilized for example to reinforce a vessel wall in a region of an aneurysm. A distal section of such a spiral element may be made of biocompatible or biosorbable material and placed around a blood vessel in an anterograde blunt dissection. Thereafter, a proximal portion of the instrument may be detached from the distal "constraint" section leaving the "constraint" in place around a portion of the blood vessel. The method of placing such a "constraint" may include the insufflation of the plane around the blood vessel to allow endoscopic viewing of the helical placement of.

From the foregoing, it can be seen that instruments and methods are provided for dissecting around anatomic structures in a minimally invasive procedure. It can be readily seen that spiral dissectors may manufactured in various special sizes and embodiments for bluntly dissecting around various anatomic structures, e.g., the trachea, colon, duodenum and ureter. It should be appreciated that the spiral lead dimension associated with an assembly of one or more spiral probes may range from less than 0.1 inches to more than 20 inches for different diameter spiral assemblies or different portions of a spiral assembly. Spiral assemblies with lesser spiral lead dimensions generally are associated with applications that favor helical penetrating forces over axial penetrating forces. Conversely, greater spiral lead dimensions are suitable for applications suited for more axial, rather than helical, penetrating forces, e.g., as when connective tissues in a plane are insubstantial.

This disclosure is illustrative and not limiting. Although specific features of the invention are shown in some drawings and not in others, this is for convenience only and any feature may be combined with another in accordance with the invention and are intended to fall within the scope of the appended claims.

What is claimed is:

1. An instrument comprising:
   a spiral assembly having at least one spiral element extending helically in at least a partial convolution around a longitudinal axis and defining an axial bore and at least one spiral gap between convolutions, each said at least one spiral element having a proximal region, a medial region, and a distal region with a blunt distal tip, wherein said blunt distal tip of each of said at least one spiral element is radially offset from the longitudinal axis so that rotation about the axis will dissect a helical path in an interior of a body.

2. The instrument of claim 1, further including a path-expanding structure mechanically coupled to said proximal, medial or distal region of each said at least one spiral element for expanding said path.

3. The instrument of claim 2, wherein said path-expanding structure comprises a varying cross-sectional dimension associated with each said at least one spiral element, said cross-sectional dimension in at least a portion of said medial or proximal region being greater than a cross-sectional dimension at said distal region thereof.

4. The instrument of claim 2, wherein said path-expanding structure comprises a bow member with at least one resilient bow element extending along said spiral axis of each said spiral element.

5. The instrument of claim 2, wherein each said path-expanding structure comprises a sleeve having a fluid-tight internal chamber containing a fluid medium.

6. The instrument of claim 2, further comprising:
   an inflatable structure having an inflation chamber and carried by said medial or distal region of each said at least one spiral element and in a contracted state having a transverse dimension about equal to a transverse dimension of said spiral element and in an expanded state having a transverse dimension greater than that of said contracted state; and an inflation mechanism operatively connected to each said inflation chamber thereby to inflate and deflate each said inflatable structure between said contracted and expanded states.

7. The instrument of claim 6, wherein said inflatable structure extends along a medial and distal region of each said at least one element.

8. The instrument of claim 6, wherein said inflation mechanism includes a pulse mechanism for pulsing an inflation medium within said inflation chamber.

9. The instrument of claim 1, wherein said at least one spiral assembly defines an outer periphery having a transverse dimension there across, wherein the transverse dimensions's larger in a medial or proximal portion of the spiral assents than in a distal portion of the spiral assembly.

10. The instrument of claim 1, wherein each at least one said spiral element has a spiral axis defining a spiral lead dimension, the spiral lead dimension in the medial or proximal portion of said spiral assembly varying from the spiral lead dimension in the distal portion thereof.

11. The instrument of claim 10, wherein said spiral lead dimension is from 0.1" to 20".

12. The instrument of claim 1, further comprising:

a bow member with at least one flexible bow element carried around said medial or distal region of each said spiral element and in a contracted state having a transverse dimension about equal to a transverse dimension of said spiral element and in an expanded state having a transverse dimension greater than that of said contracted state; and a flexing mechanism operatively connected to each said bow element thereby to flex said bow member between said contracted and expanded states.

13. The instrument of claim 1, wherein said at least one spiral element defines an interior lumen communicating between said proximal and distal regions thereof.

14. The instrument of claim 1, wherein said at least one spiral gap has a spiral gap dimension that varies and decreases in the proximal direction.

15. The instrument of claim 1, wherein each said spiral gap carries an incising structure.

16. The instrument of claim 1, wherein said axial bore has a transverse dimension, the transverse dimension of a medial or proximal portion of said axial bore being greater than the transverse dimension of a distal portion thereof.

17. The instrument of claim 1, wherein each said distal tip is angled radially inward toward said axis.

18. The instrument of claim 1, further comprising a handle member adapted for detachable coupling to said proximal, medial or distal region of each said spiral element.

19. The instrument of claim 1, wherein said spiral assembly is at least partly of transparent material.

20. A method for dissecting connective tissues, comprising the steps of:

introducing a blunt distal tip of at least one elongate spiral element into a plane proximate to an anatomic structure in an interior of a body in a first location; and advancing helically and anterograde said at least one spiral element within said plane to a second remote location thereby bluntly dissecting connective tissues in at least one spiral path in said plane.

21. The method of claim 20, wherein the introducing step is preceded by the step of inserting a stent into a lumen in said anatomic structure, said stent being selected from a group including a rigid stent, a semi-flexible stent and a stent having adjustable flexibility.

22. The method of claim 20, contemporaneously with or subsequent to the advancing step, the step of:

guiding the anterograde or retrograde movement of a path-expanding structure along each said spiral path, said path-expanding structure having a transverse dimension greater than a transverse dimension of said spiral path thereby bluntly dissecting connective tissues in said plane between said first and second locations.

23. The method of claim 20, contemporaneously with or subsequent to the advancing step, the step of:

guiding the anterograde or retrograde movement of a path-expanding portion of a spiral element along each said spiral path, said path-expanding portion comprising a proximal or medial region of each said spiral element that has a spiral lead that is greater or less than a spiral lead in said distal region thereof.

24. The method of claim 20, contemporaneously with or subsequent to the advancing step, the step of:

inserting at least one endoscopic instrument into said axial bore and treating tissue therein which includes endoscopically viewing tissue.

25. The method of claim 20, contemporaneously with or subsequent to the advancing step, the step of insufflating said plane proximate said anatomic structure.

26. The method of claim 20 wherein said anatomic structure is a blood vessel having at least one branch vessel, said advancing step further comprising the steps of:

capturing each said branch vessel in a spiral gap between convolutions of each said spiral element; and transecting each said branch vessel with an incising structure associated with a proximal portion of each said spiral gap caused by the helical advancement of said at least one spiral element.

27. The method of claim 20 wherein said anatomic structure is a blood vessel having at least one branch vessel, further comprising the step of:

introducing a distal end of a dissecting instrument into an interface between said outer periphery of said at least one spiral element and a surrounding tissue layer and dividing each said branch vessel.

28. The method of claim 20, further comprising the step of:

capturing said anatomic structure in said axial bore and removing said anatomic structure from said interior of said body upon withdrawal of said at least one spiral element from said body.

29. The method of claim 20, further comprising the steps of:

withdrawing said at least one spiral element from said interior of said body, insufflating said plane proximate to said anatomic structure; and performing a surgical treatment in said plane with endoscopic instruments.

* * * * *